United States Patent
Mahabob

(10) Patent No.: US 11,865,153 B1
(45) Date of Patent: Jan. 9, 2024

(54) TOPICAL SKIN CREAM

(71) Applicant: KING FAISAL UNIVERSITY, Al-Ahsa (SA)

(72) Inventor: Nazargi Mahabob, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/241,540

(22) Filed: Sep. 1, 2023

Related U.S. Application Data

(62) Division of application No. 18/197,787, filed on May 16, 2023.

(51) Int. Cl.

| | |
|---|---|
| *A61K 36/47* | (2006.01) |
| *A61K 9/06* | (2006.01) |
| *A61K 47/38* | (2006.01) |
| *A61K 47/12* | (2006.01) |
| *A61K 47/14* | (2017.01) |
| *A61K 47/26* | (2006.01) |
| *A61K 9/00* | (2006.01) |
| *A61K 36/738* | (2006.01) |
| *A61K 47/10* | (2017.01) |

(52) U.S. Cl.
CPC ............ *A61K 36/47* (2013.01); *A61K 9/0014* (2013.01); *A61K 9/06* (2013.01); *A61K 36/738* (2013.01); *A61K 47/10* (2013.01); *A61K 47/12* (2013.01); *A61K 47/14* (2013.01); *A61K 47/26* (2013.01); *A61K 47/38* (2013.01)

(58) Field of Classification Search
None
See application file for complete search history.

(56) References Cited

U.S. PATENT DOCUMENTS 9,610,236 B2   4/2017   Danchin et al.

FOREIGN PATENT DOCUMENTS

MY          184354 A       4/2021

OTHER PUBLICATIONS

M Laut et al. (Cutaneous wound healing activity of herbal ointment containing the leaf extract of Acalypha indica L on mice, Journal of Physics: Conference Series 1146; 2019) (Year: 2019).*
Mahboubi (Rosa damascene as a holy ancient herb with novel applications, Journal of Traditional and Complementary Medicine 6 (2016) 10-16). (Year: 2016).*
Ibrahim, A. M., "In Vitro Evaluation and Wound Healing Cream Formulation Of Acalypha Indica Linn Ethanolic Extract," Universiti Teknologi Malaysia Jan. 2016.
Laut. M., et al., "Cutaneous wound healing activity of herbal ointment containing the leaf extract of Acalypha indica L. on mice (*Mus musculus*)", IOP Conf. Series: Journal of Physics: Conf. Series 1146:012025 (2019).
Ishak, F. D., et al., "In Vitro Study of Antimicrobial Activity of Acalypha Indica Linn. Extract", The Open Conference Proceedings Journal 4 (Suppl-2, M14): pp. 57-60 (2013).
Selvamani, S. et al., "Antibacterial and antifungal activities of different organic solvent extracts of Acalypha indica (Linn.)", Asian Journal of Plant Science and Research, 5(5): pp. 52-55 (2015).
Govindarajan, M. et al., "Antibacterial activity of Acalypha indica L.", 12: pp. 299-302 (2008).

* cited by examiner

*Primary Examiner* — Melissa S Mercier
(74) *Attorney, Agent, or Firm* — Nath, Goldberg & Meyer; Richard C. Litman

(57) ABSTRACT

A topical skin cream is provided. The topical skin cream includes *Acalypha indica* oil, *Rosa damascena* Mill oil, at least one emulsion stabilizer, at least one exfoliant, at least one preservative, and water. In an embodiment, the topical skin cream may include *Acalypha indica* oil, *Rosa damascena* Mill oil, hydroxypropylmethyl cellulose, polyethylene glycol, sucrose, an alpha-hydroxy acid, water, and at least one preservative. The topical skin cream can be used to treat various skin related problems, including but not limited to treatment of acne, fungal infections, skin allergies, and other skin conditions.

3 Claims, No Drawings

TOPICAL SKIN CREAM

CROSS-REFERENCE TO RELATED APPLICATION

This application is a divisional of U.S. patent application Ser. No. 18/197,787, filed on May 16, 2023.

BACKGROUND

1. Field

The disclosure of the present patent application relates to a topical skin cream, and particularly to a topical skin cream including *Acalypha indica* oil and *Rosa damascena* Mill oil.

2. Description of the Related Art

The American Academy of Dermatology Association reports that acne is the most common skin condition in the United States, affecting up to 50 million Americans annually; meanwhile, 1 in 10 people will develop atopic dermatitis during their lifetime, 7.5 million people in the United States alone have psoriasis, and 16 million have rosacea. Meanwhile, fungal skin infections are considered the most common global issue for skin health. Existing topical treatments for these ailments suffer from a variety of well-characterized deficiencies, including at least poor retention and low bioavailability.

Thus, a topical skin cream solving the aforementioned problems is desired.

SUMMARY

The topical skin cream may include a composition comprising *Acalypha indica* oil, *Rosa damascena* Mill oil, at least one emulsion stabilizer, at least one exfoliant, at least one preservative, and water. In an embodiment, the topical skin cream may include *Acalypha indica* oil, *Rosa damascena* Mill oil, hydroxypropylmethyl cellulose, polyethylene glycol, sucrose, an alpha-hydroxy acid, water, and at least one preservative. The topical skin cream can be used for various skin related problems, including but not limited to treatment of acne, fungal infections, skin allergies, and other skin conditions.

In an embodiment the topical skin cream composition may include between about 15% and about 25% *Acalypha indica* oil and between about 0.5% and about 1.5% *Rosa damascena* Mill oil. In a particular embodiment, the topical skin cream may include about 20% *Acalypha indica* oil and about 10% *Rosa damascena* Mill oil. In a further embodiment, the topical skin cream may include about 3% hydroxypropylmethyl cellulose, about 10% polyethylene glycol, about 2% sucrose, about 0.05% sodium citrate, about 0.2% citric acid, and about 0.2% methylparaben. In certain embodiments, the remainder of the composition will be water.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

*Acalypha indica* is an erect annual herb that grows widely throughout the World and is particularly common in tropical climates. In Africa, it occurs in Nigeria in West Africa, throughout tropical Africa, and in the Indian Ocean islands. It also occurs in India, Southeast Asia, Yemen, and Oceania. The plant has many traditional medicinal uses. An oil may be derived from the freshly plucked leaves using any known distillation method, including but not limited to steam distillation.

*Rosa damascena* Mill is a rose hybrid derived from *Rosa gallica* and *Rosa moschata*. The flowers of *Rosa damascena* Mill are known for their fine fragrance and are commercially harvested and distilled to produce rose oil.

Thus, the topical skin cream may include a composition comprising *Acalypha indica* oil, *Rosa damascena* Mill oil, at least one emulsion stabilizer, at least one exfoliant, at least one preservative, and water. In an embodiment, the topical skin cream may include *Acalypha indica* oil, *Rosa damascena* Mill oil, hydroxypropylmethyl cellulose, polyethylene glycol, sucrose, an alpha-hydroxy acid, water, and at least one preservative. The topical skin cream can be used for treating various skin related problems, including but not limited to treatment of acne, fungal infections, skin allergies, and other skin conditions.

In an embodiment, die topical skin cream composition may include between about 15% and about 25% *Acalypha indica* oil and between about 0.5% and about 1.5% *Rosa damascena* Mill oil. In a particular embodiment, the topical skin cream composition may include about 20% *Acalypha indica* oil and about 1% *Rosa damascena* Mill oil. In a further embodiment, the topical skin cream composition may additionally include about 3% hydroxypropylmethyl cellulose, about 10% polyethylene glycol, about 2% sucrose, about 0.05% sodium citrate, about 0.2% citric acid, and about 0.2% methylparaben. In an embodiment, the remainder of the composition can comprise water.

In certain embodiments, the topical skin cream composition may be formulated as a gel, which may be particularly suited to facial applications.

The at least one emulsion stabilizer may include any emulsion stabilizer known for use in cosmetics, including but not limited to sodium lauryl sulfate, a lacylate, a glutamate, polyethylene glycol, a quaternium ammonium compound, a Tween, hydroxypropylmethyl cellulose, or any combination thereof. In an embodiment, the at least one emulsion stabilizer may comprise hydroxypropylmethyl cellulose. In a further embodiment, the at least one emulsion stabilizer may comprise polyethylene glycol. In a particular embodiment, the at least one emulsion stabilizer may comprise both hydroxypropylmethyl cellulose and polyethylene glycol.

The at least one exfoliant may include any exfoliant known for use in cosmetics, including but not limited to physical exfoliants such as ground walnut, ground apricot pits, or pumice crystals, and chemical exfoliants such as alpha-hydroxy acids, beta-hydroxy acids, a sugar, or any combination thereof. In an embodiment, the at least one exfoliant may include an alpha-hydroxy acid. In a further embodiment, the at least one exfoliant may include sucrose. In a particular embodiment, the at least one exfoliant may include both sucrose and an alpha-hydroxy acid.

The at least one preservative may be any preservative known as being suitable for use in cosmetics, including but not limited to organic acids, alcohols and phenols, parabens, urea compounds, formaldehyde releasing preservatives, isothiazolines, quaternary ammonium compounds, and any combination thereof. In an embodiment, the at least one preservative may include methylparaben. In a further embodiment, the at least one preservative may include propylparaben. In yet a still further embodiment, the at least one preservative may include sodium citrate Mixtures of any of these preservatives may be contemplated herein.

In an embodiment, the topical skin cream composition may be made by dispersing an emulsion stabilizer in heated water; adding any additional emulsion stabilizers, the at least one exfoliant, and the at least one preservative to form a first mixture; once those are thoroughly mixed slowly adding the *Acalypha indica* oil and the *Rosa damascena* Mill oil to form the topical skin cream and allowing the topical skin cream to cool to room temperature. In an embodiment, the method may further include adding sodium citrate to the first mixture to form a second mixture and adding the *Acalypha indica* oil and the *Rosa damascena* Mill oil to the second mixture to form the topical skin cream. In another embodiment, the initial heating may be conducted until the water reaches a temperature of about 60° C. to about 80° C., about 65° C. to about 75° C., or about 70° C. In another embodiment, this temperature may be maintained until the final cooling step.

In an embodiment, the topical skin cream composition may be made by dispersing hydroxypropylmethyl cellulose in heated water; adding polyethylene glycol-400, sucrose, citric acid, and methylparaben thereto to create a first mixture; adding an aqueous solution of sodium citrate to the first mixture to form a second mixture; adding *Acalypha indica* oil and *R. Damascena* Mill oil to the second mixture to produce the topical skin cream, and allowing the topical skin cream to cool to room temperature.

In a further embodiment, the final composition of the topical skin cream may include about 3% hydroxypropylmethyl cellulose, about 10% polyethylene glycol-400, about 2% sucrose, about 0.2% citric acid, about 0.2% methylparaben, about 0.05% sodium citrate, about 20% *Acalypha indica* oil, and about 1% *R. Damascena* Mill oil. In another embodiment, the remainder of the topical skin cream may be water.

The topical skin cream composition may be used to treat a skin condition by applying the topical skin cream composition directly to the skin of a subject in need thereof. In certain embodiments, the skin condition to be treated may be acne, a fungal infection, a skin allergy, or the like. In other embodiments, the topical skin cream composition may be applied to a subject to condition skin of the subject. In a further embodiment, the topical skin cream composition may be applied to a subject to treat atopic dermatitis, psoriasis, or the like in the subject.

The topical skin cream may be better understood in view of the following examples.

Example 1

Synthesizing the Topical Skin Cream

Hydroxypropylmethyl cellulose (HPMC K 14 3% by weight) was dispersed in 50 ml of distilled water maintained at 70° C. for 20 min using a magnetic stirrer. Then polyethylene glycol-400 (10% by weight), sucrose (2% by weight), citric acid (0.2% by weight), and methylparaben (0.2% by weight) were added with stirring to create a first mixture. Thereafter sodium citrate was dissolved in 10 ml of distilled water and added (0.05% by weight) to the first mixture to form a second mixture Finally, *Acalypha indica* oil (20% by volume) and *R. Damascena* Mill oil (1% by volume) were slowly added under mixing to produce the topical skin cream. The topical skin cream was then allowed to cool to room temperature, forming a gel or cream. The thus produced composition has the following composition.

| Ingredient | (%) |
| --- | --- |
| Acalypha Indica | 20 |
| Rose Oil | 1 |
| HPMCK 14 | 3 |
| PEG400 | 10 |
| Sucrose | 2 |
| Sodium citrate | 0.05 |
| Citric Acid | 0.2 |
| Methyl Paraben | 0.2 |
| Water | q.s. to 100 |

It is to be understood that the topical skin cream is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of making a topical skin cream composition, comprising:

dispersing an emulsion stabilizer in heated water;

adding at least one exfoliant and at least one preservative to the heated water to obtain a first mixture;

adding *Acalypha indica* oil and *Rosa damascena* Mill oil to the first mixture to obtain the topical skin cream composition; and allowing the topical skin cream composition to cool to room temperature.

2. The method of claim 1, further comprising:

adding aqueous sodium citrate to the first mixture;

prior to adding the *Acalypha indica* oil and the *Rosa damascena* Mill oil to the first mixture to form the topical skin cream composition.

3. The method of claim 2, wherein:

the emulsion stabilizer includes hydroxypropylmethyl cellulose;

and polyethylene glycol-400, the at least one exfoliant includes sucrose, and the at least one preservative includes citric acid and methylparaben.

* * * * *